(12) United States Patent
Tachizaki et al.

(10) Patent No.: US 6,901,129 B2
(45) Date of Patent: May 31, 2005

(54) X-RAY COMPUTER TOMOGRAPHY APPARATUS

(75) Inventors: Hisashi Tachizaki, Irvine, CA (US); Masahiro Kazama, Shioya-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/188,050

(22) Filed: Jul. 3, 2002

(65) Prior Publication Data

US 2003/0016778 A1 Jan. 23, 2003

(30) Foreign Application Priority Data

Jul. 4, 2001 (JP) ........................................ 2001-202870
Jul. 2, 2002 (JP) ........................................ 2002-193254

(51) Int. Cl.[7] ................................................. A61B 6/00
(52) U.S. Cl. ........................................... 378/4; 378/901
(58) Field of Search ............................... 378/4–20, 901, 378/116

(56) References Cited

U.S. PATENT DOCUMENTS

| | | | | |
|---|---|---|---|---|
| 5,103,469 A | | 4/1992 | Tanaka | ........................ 378/16 |
| 5,822,393 A | * | 10/1998 | Popescu | ...................... 378/108 |
| 6,094,468 A | * | 7/2000 | Wilting et al. | .................. 378/8 |
| 6,236,705 B1 | * | 5/2001 | Stergiopoulos et al. | ........ 378/8 |
| 6,307,912 B1 | * | 10/2001 | He et al. | ...................... 378/19 |

FOREIGN PATENT DOCUMENTS

| | | |
|---|---|---|
| JP | 61-52860 | 3/1986 |
| JP | 5-305077 | 11/1993 |
| JP | 2001-43993 | 2/2001 |

* cited by examiner

*Primary Examiner*—Craig E. Church
*Assistant Examiner*—Jurie Yun
(74) *Attorney, Agent, or Firm*—Oblon, Spivak, McClelland, Maier & Neustadt, P.C.

(57) ABSTRACT

An X-ray absorptance map associated with an object to be examined is generated on the basis of scanogram data obtained from a predetermined direction of the object, and imaging conditions are determined on the basis of the absorptance map. Before tomography, an index representing a radiation dose in the execution of scan in accordance with the imaging conditions is calculated and displayed, together with the imaging conditions. Every time the imaging conditions are changed, an index representing a radiation dose is calculated and displayed. Tomography is executed in accordance with the finally determined imaging conditions. This makes it possible to reduce the radiation dose to the object and obtain a tomographic image with high quality.

7 Claims, 7 Drawing Sheets

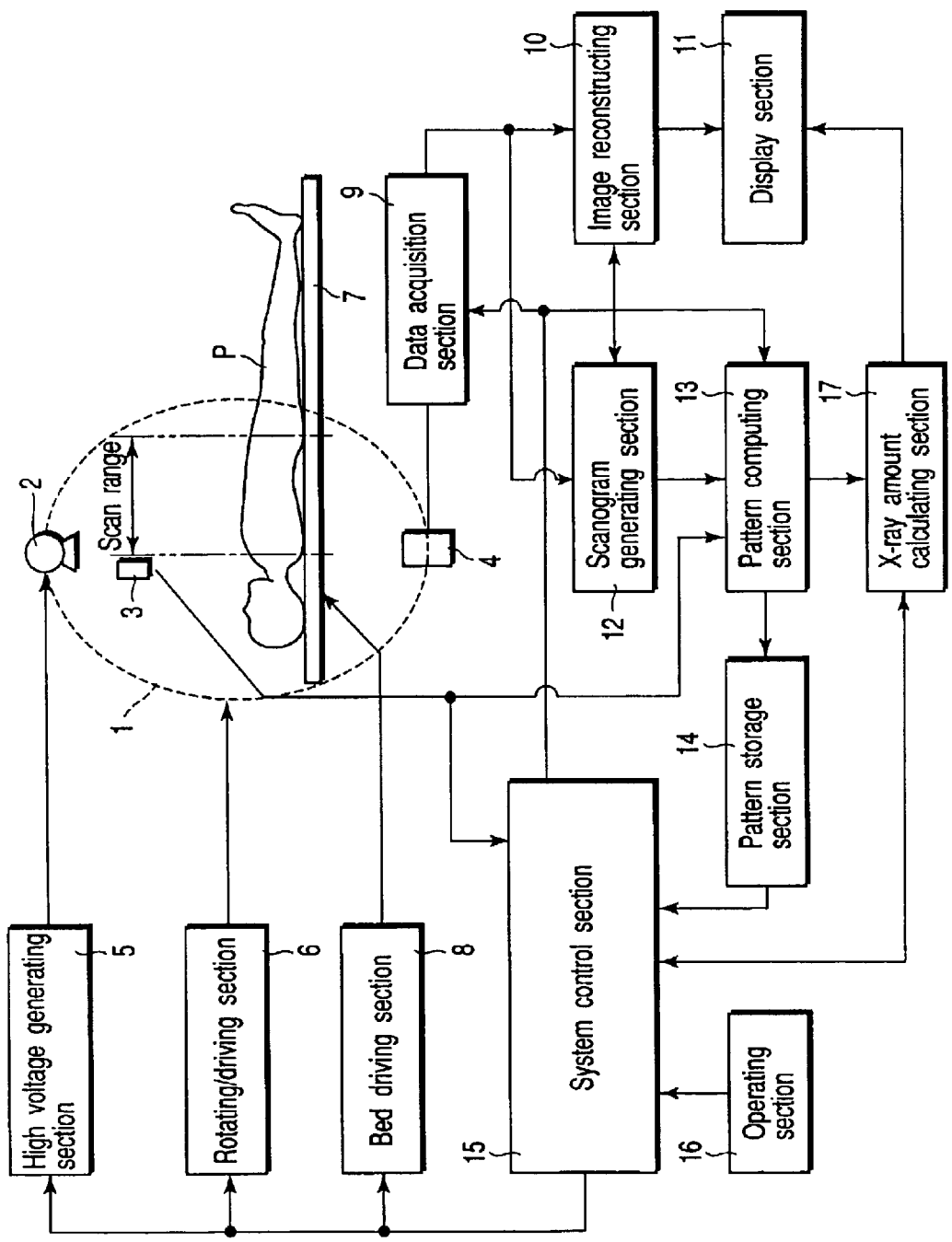
F I G. 5

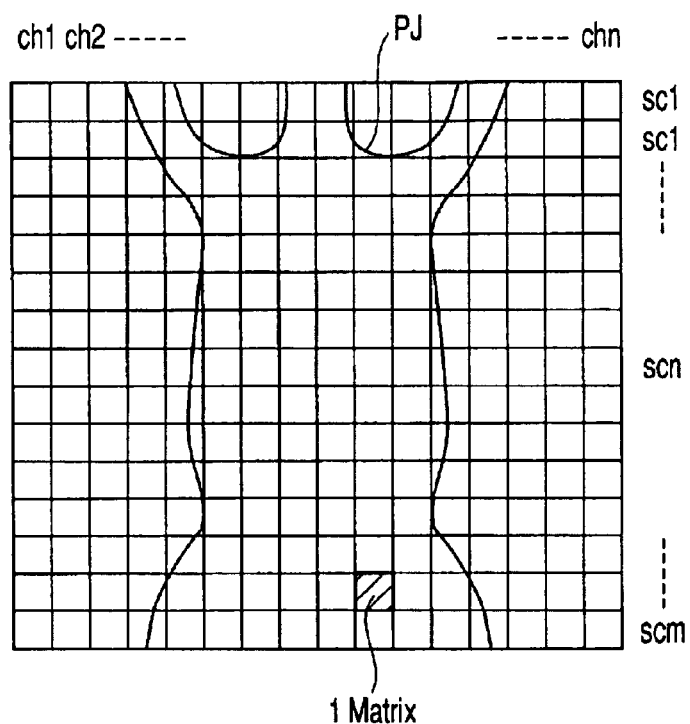
F I G. 6
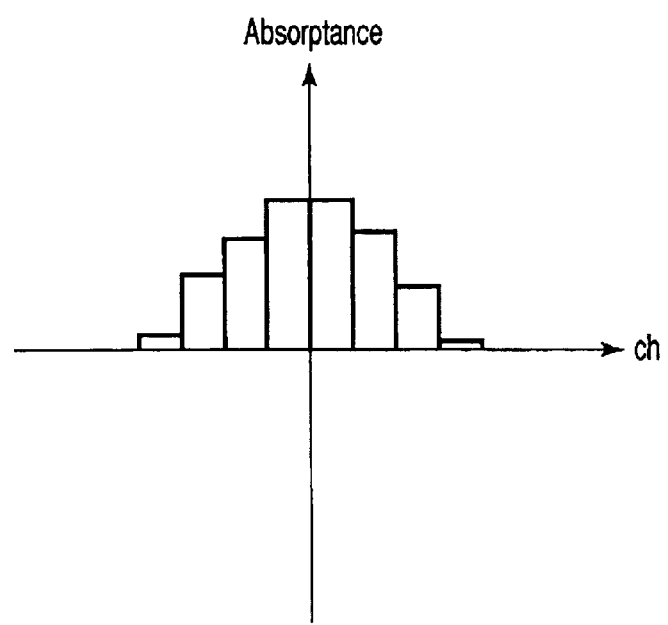
F I G. 7

X-RAY COMPUTER TOMOGRAPHY APPARATUS

CROSS-REFERENCE TO RELATED APPLICATIONS

This application is based upon and claims the benefit of priority from the prior Japanese Patent Application No. 2001-202870, filed Jul. 4, 2001, the entire contents of which are incorporated herein by reference.

BACKGROUND OF THE INVENTION

1. Field of the Invention

The present invention relates to an X-ray computer tomography apparatus which dynamically changes an imaging condition during a scan on the basis of the scanogram data obtained by scanography executed before the start of the scan.

2. Description of the Related Art

X-ray computer tomography apparatuses (to be referred to as "X-ray CT apparatuses" hereinafter) have made remarkable progress after they were invented. Recently, X-ray CT apparatuses have been put into practice, which allow imaging schemes such as helical scan in which an object to be examined is helically irradiated with X-rays by helically and continuously rotating an X-ray tube while moving an object to be examined in the body axis direction and multi-slice scan which can execute tomography with respect to a plurality of slices by using a plurality of detection arrays. It may safely be said that such progress in X-ray CT apparatuses is the result of relentless challenges to an improvement in image quality, reductions in imaging time and image reconstruction time, a reduction in X-ray dose, and the like.

A general X-ray CT apparatus called a third-generation apparatus performs tomography by the following procedure. First of all, an X-ray tube and multi-channel X-ray detector are arranged to oppose each other through an object to be examined. The object is then irradiated with an X-ray beam from the X-ray tube while the X-ray and X-ray detector are rotated around the object through 360°. The X-rays transmitted through the object are detected by the X-ray detector. At this time, the intensity of X-rays emitted from the X-ray tube is constant (i.e., the tube voltage and tube current in the X-ray tube are constant). Note that the X-rays emitted from the focal point of the X-ray tube is collimated into a fan-shaped X-ray beam. The spread width of an X-ray beam is determined in accordance with a slice thickness and the like.

A set of projection data detected by the X-ray detector at a given rotational angle centered on the body axis of an object to be examined is called a view. Measurement of the amounts of X-rays transmitted in a plurality of view directions which is done while the X-ray and X-ray detector are rotated around the body axis of the object is called scan. By performing reconstruction processing for the projection data of a plurality of views obtained by this scan using a high-speed arithmetic unit or the like, a tomographic image of the object can be obtained.

A cross-section of the human body taken from a chest portion to a waist portion can be regarded as a nearly elliptic shape, as shown in FIG. 1. When, therefore, the human body is imaged by an X-ray CT apparatus, the detected amount of X-ray transmitted varies depending on the emission angle. This is because the amount of X-rays absorbed by an object P to be examined when the object is irradiated with X-rays from an angular position θ1 (the major-axis direction of the ellipse) differs from that absorbed by the object when the object is irradiated with X-rays from an angular position θ2 (the minor-axis direction of the ellipse). In particular, the detected amount of X-rays transmitted on the plane side of the human pelvis portion or the like considerably differs from that on the side surface side.

FIG. 2 is a graph showing the relationship between the angular position of the X-ray tube and the amount of X-rays transmitted in a case wherein the human body is imaged by a conventional X-ray CT apparatus. The abscissa represents the emission angle of X-rays with respect to the object P (i.e., the angular position of the X-ray tube); and the ordinate, the amount of X-rays transmitted. As is obvious from FIG. 2, the amount of X-rays transmitted in the major-axis direction θ1 of the ellipse is smaller than that in the minor-axis direction θ2 of the ellipse. In addition, the amount of X-rays transmitted periodically changes along the entire circumference of the object P regarded as an elliptic shape.

Variations in the amount of X-rays transmitted with respect to this X-ray emission angle cause variations in S/N ratio with respect to the emission angle. That is, the S/N ratio is high at a portion where the amount of X-rays transmitted is large, whereas the S/N ratio is low at a portion where the amount of X-rays transmitted is small. Consequently, when a tomographic image is to be generated from views obtained by this scan, the overall S/N ratio of the tomographic image becomes low.

In order to solve this problem, for example, the following two techniques are conceivable.

One is a technique of increasing the overall S/N ratio of an image by increasing the amount of X-rays transmitted as a whole. In order to realize this, the intensity of X-rays to be emitted must be increased. In this case, however, an excessive amount of X-rays is applied to a portion originally having a high S/N ratio. This therefore causes an increase in radiation dose.

The other is a technique of increasing the overall S/N ratio of an image by controlling the tube voltage or tube current in the X-ray tube in accordance with the rotational angle (X-ray emission angle) of the X-ray tube. With this technique, the object P can be scanned with a constant amount of X-rays transmitted on one slice. This technique is effective in obtaining a tomographic image of one slice. If, however, tomography is continuously executed many times by helical scan as in recent years, the radiation dose cannot be satisfactorily reduced. This is because, as shown in FIG. 3, the object P has uneven thickness in the body axis direction, so that the amount of X-rays transmitted at a given portion is large while that at another portion is small depending on the position of the object P in the body axis direction.

Recently, further improvements have been made on the latter technique. For example, a technique of making the amounts of X-rays transmitted in the respective angular directions around an object to be examined and at the respective positions in the body axis direction almost uniform in an X-ray CT apparatus designed to perform helical scan has been proposed by Tanaka (Japanese Patent No. 2768932). According to this technique, scanography is executed in two directions with different rotational angles (e.g., plane direction and side surface direction) before tomography by helical scan, and a proper X-ray emission amount pattern is estimated from this scanography. In executing helical scan or the like, the tube current in the X-ray tube is controlled to make the amount of X-rays emitted from the X-ray tube coincide with the estimated pattern in accordance with the rotational angle of the X-ray tube with respect to the object and the position of the X-ray tube in the body axis direction. Note that scanography is an imaging method in which an X-ray tube is translated relative to an object to be examined in the body axis direction while X-rays are emitted in a state wherein the X-ray tube is fixed at a predetermined angular position with respect to the object, and the amount of X-rays transmitted is detected by an X-ray detector.

In the above improved technique, however, in order to obtain a proper X-ray emission amount pattern in helical scan, scanography must be executed twice. This therefore increases the radiation dose to the object. In addition, since scanography must be executed twice, the operation efficiency deteriorates.

It is, therefore, an object of the present invention to provided an X-ray CT apparatus which reduces the radiation dose to an object to be examined and improves operation efficiency and image quality by determining proper imaging conditions and executing scan in accordance with the determined conditions.

BRIEF SUMMARY OF THE INVENTION

In order to achieve the above object, the present invention provides the following means.

According to the first aspect of the present invention, an X-ray computer tomography apparatus comprises an X-ray source which emits X-rays, an X-ray detector which has a plurality of detection elements configured to detect X-rays transmitted through an object to be examined, a scanogram generating section which generates a scanogram in a first direction of the object on the basis of an output from the X-ray detector, a distribution information generating section which generates distribution information of X-ray absorptances or absorbed X-ray doses in the first direction of the object by dividing the scanogram into matrixes and calculating X-ray absorptances or absorbed X-ray doses on a matrix basis, an imaging condition determining section which determines an imaging condition on the basis of the distribution information, and a controller which controls computer tomography of the object on the basis of the imaging condition.

According to another aspect of the present invention, an X-ray computer tomography apparatus comprises an X-ray source which emits X-rays, an X-ray detector which has a plurality of detection elements configured to detect X-rays transmitted through an object to be examined, a scanogram generating section which generates at least one scanogram associated with the object on the basis of an output from the X-ray detector, a size determining section which determines a size of the object on the basis of at least one scanogram, an imaging mode selecting section which selects, in accordance with the determined size of the object, a first imaging mode of emitting a first amount of X-rays or a second imaging mode of emitting a second amount of X-rays which is smaller than the first amount of X-rays, and a controller which controls computer tomography of the object on the basis of the selected imaging mode.

According to still another aspect of the present invention, an X-ray computer tomography apparatus comprises an X-ray source which emits X-rays, an X-ray detector which has a plurality of detection elements configured to detect X-rays transmitted through an object to be examined, a scanogram generating section which generates at least one scanogram associated with the object on the basis of an output from the X-ray detector, a memory which stores a plurality of recommended imaging conditions corresponding to each object size, a size determining section which determines a size of the object on the basis of at least one scanogram, a selecting section which selects an imaging condition corresponding to the determined size of the object from the plurality of recommended imaging conditions, and a display device which displays information which prompts to set the selected imaging condition.

According to still another aspect of the present invention, an X-ray computer tomography apparatus comprises an X-ray source which emits X-rays, an X-ray detector which has a plurality of detection elements configured to detect X-rays transmitted through an object to be examined, a scanogram generating section which generates a scanogram of the object on the basis of an output from the X-ray detector, an imaging condition determining section which determines an imaging condition associated with computer tomography of the object on the basis of a scanogram in a first direction of the object, an X-ray amount calculating section which calculates a radiation dose to the object or a total amount of X-rays emitted from the X-ray source on the basis of the imaging condition, and a display device which displays the calculated radiation dose or the total X-ray amount before the computer tomography.

BRIEF DESCRIPTION OF THE SEVERAL VIEWS OF THE DRAWING

FIG. 5 is a schematic view showing the arrangement of the X-ray CT apparatus according to the first embodiment;

FIG. 6 is a view schematically showing an acquired scanogram;

FIG. 7 is a graph showing the X-ray absorptances in the respective matrixes corresponding to scn;

DETAILED DESCRIPTION OF THE INVENTION

The first and second embodiments of the present invention will be described below with reference to the accompanying drawings. There are various types of X-ray CT apparatuses, including, for example, a rotate/rotate type in which an X-ray tube and detector system rotate together around an object to be examined, a stationary/rotate type in which many detection elements are arrayed, and only an X-ray tube rotates around an object, and a type in which the position of an X-ray source is electronically moved above a target by deflecting an electron beam. The technical idea of the present invention can be applied to any of these types. For the sake of a specific description, each of the following embodiments will exemplify an X-ray CT apparatus of the rotate/rotate type which has currently become mainstream.

(First Embodiment)

Figure 1:
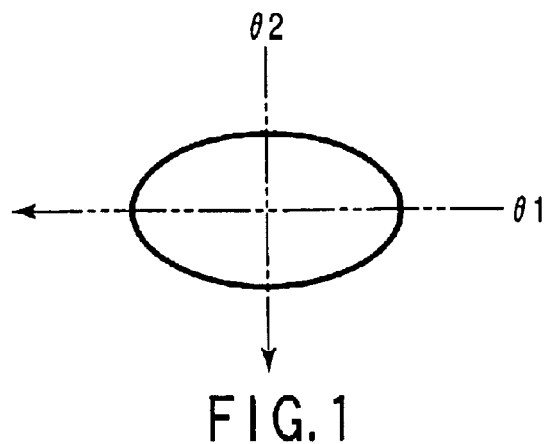
FIG. 1 is a view schematically showing a cross-section of a human body in the body axis direction.
Figure 2:
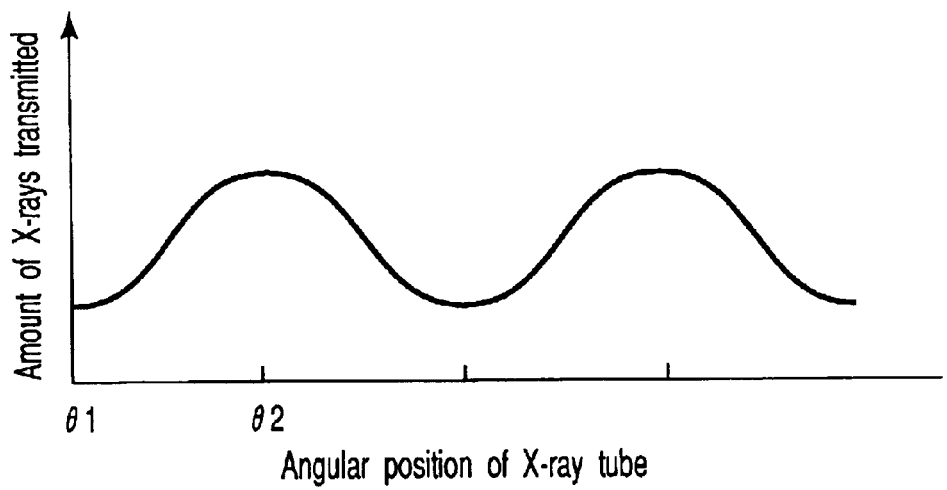
FIG. 2 is a graph showing the relationship between the angular position of an X-ray tube and the amount of X-ray transmitted in a conventional X-ray computer tomography apparatus.
Figure 3:
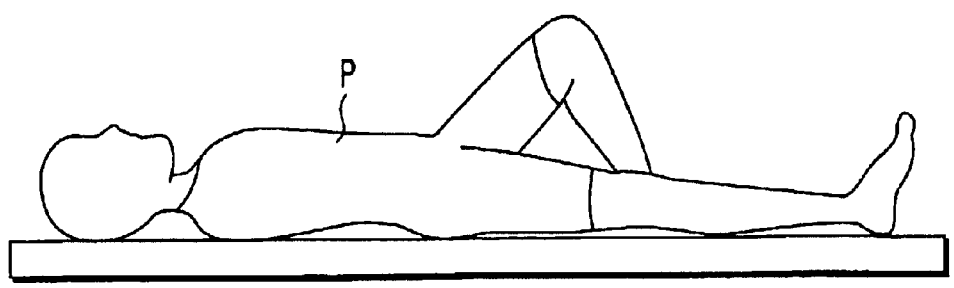
FIG. 3 is a side view schematically showing an object to be examined which lies on a bed.
Figure 4:
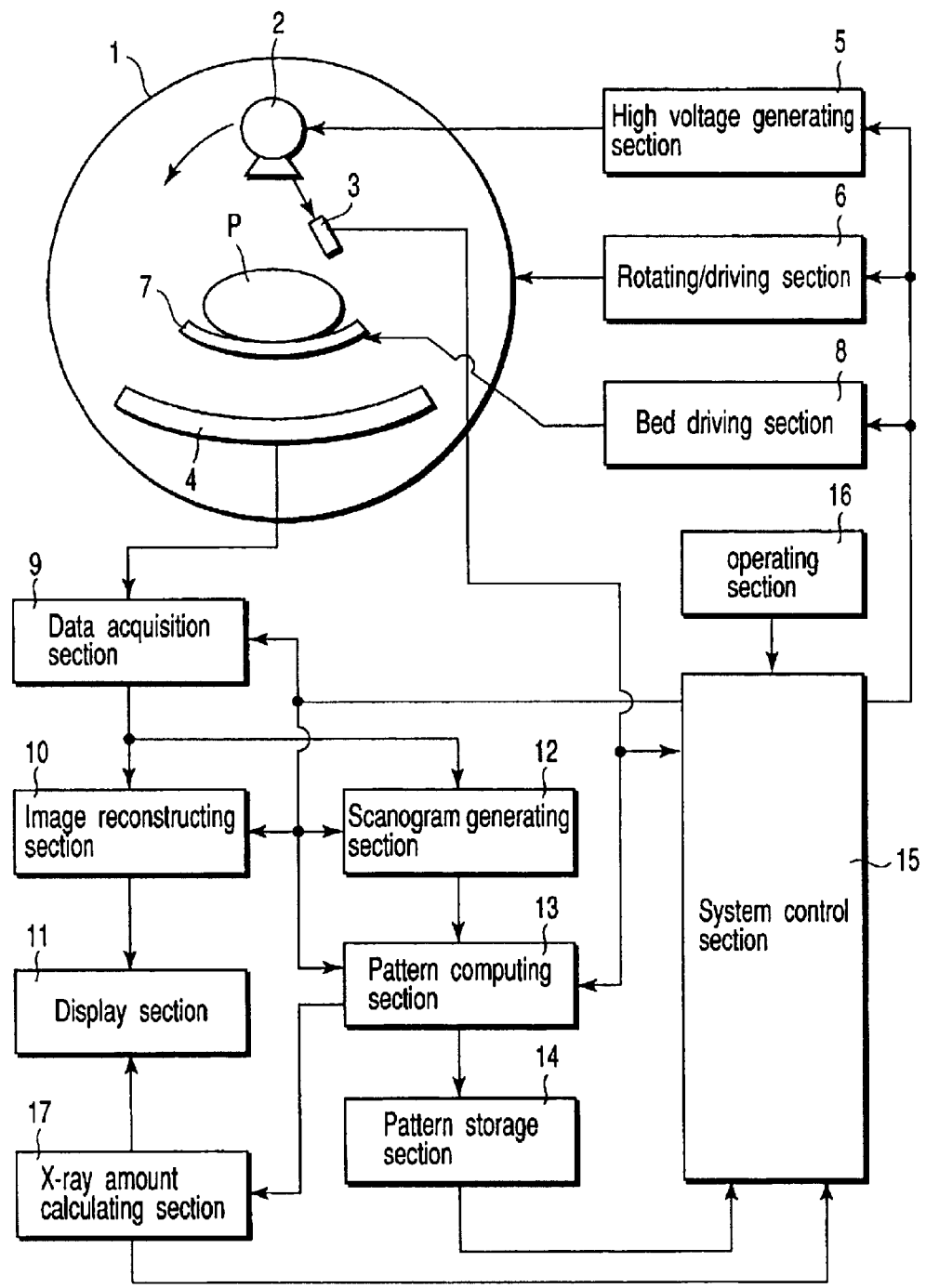
FIG. 4 is a schematic view showing the arrangement of an X-ray CT apparatus according to the first embodiment.

FIGS. 4 and 5 are views showing the schematic arrangement of an X-ray CT apparatus according to the first embodiment. FIG. 4 is a front view of a gantry 1. FIG. 5 is a side view of the gantry 1.

As shown in FIGS. 4 and 5, the X-ray CT apparatus according to this embodiment includes the gantry 1, an X-ray tube 2, a compensatory detector 3, an X-ray detector 4, a high voltage generating section 5, a rotating/driving section 6, a bed 7, a bed driving section 8, a data acquisition section 9, an image reconstructing section 10, a display section 11, a scanogram generating section 12, a pattern computing section 13, a pattern storage section 14, a system control section 15, and an operating section 16.

The gantry 1 has a rotating ring. The rotating ring has the X-ray tube 2, compensatory detector 3, and X-ray detector 4. This rotating ring is rotated/driven by the rotating/driving section 6.

The X-ray tube 2 is a vacuum tube for generating X-rays and mounted on the rotating ring of the gantry 1. Power required to emit X-rays is supplied from the high voltage generating section 5 to the X-ray tube 2 through a slip ring (not shown). The X-ray tube 2 accelerates electrons and makes them collide with a target by using the applied high voltage, thereby irradiating an object P to be examined, which is placed in an effective field of view FOV, with X-rays.

The compensatory detector 3 is a photomultiplier or TV camera, which detects the amount of X-rays before they are transmitted through the object P. The X-ray amount detected by the compensatory detector 3 is output to the pattern computing section 13 and can be used for absorptance map creation processing (to be described later).

The X-ray detector 4 is placed to oppose the X-ray tube 2 and has multi-channel X-ray detection elements (e.g., 800-channel X-ray detection elements) for detecting the amount of X-rays after they are transmitted through the object P. These X-ray detection elements are arranged in a line along the spread of an X-ray beam emitted from the X-ray tube 2. Note that if this X-ray CT apparatus is compatible with multi-slice CT, a plurality of X-ray detection element arrays are arranged parallel in the body axis direction of the object P.

The high voltage generating section 5 is designed to apply a high voltage to the X-ray tube 2 and comprised of a high-voltage transformer, filament heating converter, rectifier, high-voltage switch, and the like. The high voltage generating section 5 applies a high voltage to the X-ray tube 2 through a slip ring (not shown).

The rotating/driving section 6 performs driving control to, for example, rotate the X-ray tube 2 and X-ray detector 4 around a central axis parallel to the body axis direction of the object placed on the bed 7.

The bed driving section 8 translates the object P placed on the bed 7 in the body axis direction of the object P.

The data acquisition section 9 has a plurality of DAS chips, receives an enormous amount of data associated with all the M×N channels detected by the X-ray detector 4, and performs amplification processing, A/D conversion processing, and the like.

The image reconstructing section 10 reconstructs projection data obtained from the data acquisition section 9 to generate reconstructed image data corresponding to a predetermined slice. Note that the image reconstructing section 10 performs so-called real-time reconstruction, i.e., reconstructing a tomographic image from projection data in many directions within a shorter period of time than required to acquire projection data in many directions which are required to reconstruct one tomographic image.

The display section 11 displays a scanogram, a reconstructed CT image, various imaging conditions, the X-ray dose to an object to be examined or the total x-ray dose, and the like. The form of display of various imaging conditions and the X-ray dose to the object or the total X-ray dose will be described later.

The scanogram generating section 12 generates a scanogram by obtaining the transmission data acquired by scanography from the data acquisition section 9.

The pattern computing section 13 computes and generates a proper X-ray emission amount pattern on the basis of the scanogram data generated by the scanogram generating section 12 or projection data from the data acquisition section 9. More specifically, the pattern computing section 13 generates a tube current control pattern in accordance with the position of the X-ray tube 2 in the body axis direction of the object P and the angle of the X-ray tube 2 with respect to the body axis by approximately calculating the diameter of a virtual phantom substantially equivalent to the object P.

The pattern storage section 14 stores the X-ray emission amount pattern generated by the pattern computing section 13.

The system control section 15 has a computer serving as a central function, a memory, and the like, and organically controls each unit constituting this X-ray CT apparatus.

The operating section 16 includes a keyboard, various switches, mouse, and the like which are used by the operator to input various set values, instructions, and the like to the system control section 15.

An X-ray amount calculating section 17 calculates a radiation dose or a radiation dose index in tomography on the basis of the X-ray emission amount pattern generated by the pattern computing section 13. As a radiation dose index, a CTDIw value (Weighted Computed Tomography Dose Index to be simply referred to as a CTDI hereinafter), DLP (Dose Length Product), mAs (mA second), or the like is used.

A CTDI is a radiation dose index per reference slice thickness (e.g., 10 mm) when the X-ray tube and X-ray detector are rotated once by the rotating ring. Therefore, the CTDI is converted into a radiation dose at the reference slice thickness regardless of the slice width (e.g., 0.5 mm×8 slices, 0.5 mm×4 slices, or 10 mm×2 slices) with which tomography is performed. Such CTDI reference data are preferably stored in the form of a table in a memory (not shown) in the system control section 15. In this table, tube voltages, the sizes of imaging areas (FOVs), wedges, and CTDI reference data are preferably associated with each other. For example, a CTDI measurement value (mGy/100 mAs) per 100 mAs which corresponds to one conventional scan rotation is registered in the table in correspondence with each tube voltage, FOV, and wedge at a standard slice thickness for each type of X-ray CT apparatus.

According to another example of the table, a CTDI is measured in advance for each slice width (slice thickness× slice count) at a standard tube voltage, FOV, and wedge which are used to determine a slice width coefficient, and the slice width ratio is registered as a coefficient. In this case, a slice width coefficient is a common coefficient regardless of the tube voltage and wedge. If, for example, another slice width (0.5 mm×4 slices) is selected in an examination plan by setting a standard slice width (5 mm×4 slices) as a reference (e.g., 1.00), a coefficient (e.g., 2.00) is accumulated.

DLP is an index representing the total radiation dose in a scan range and calculated on the basis of a CTDI.

mAs is an index representing the total tube current value in a scan time and is calculated from the tube current and irradiation time set in an examination plan.

Figure 9:
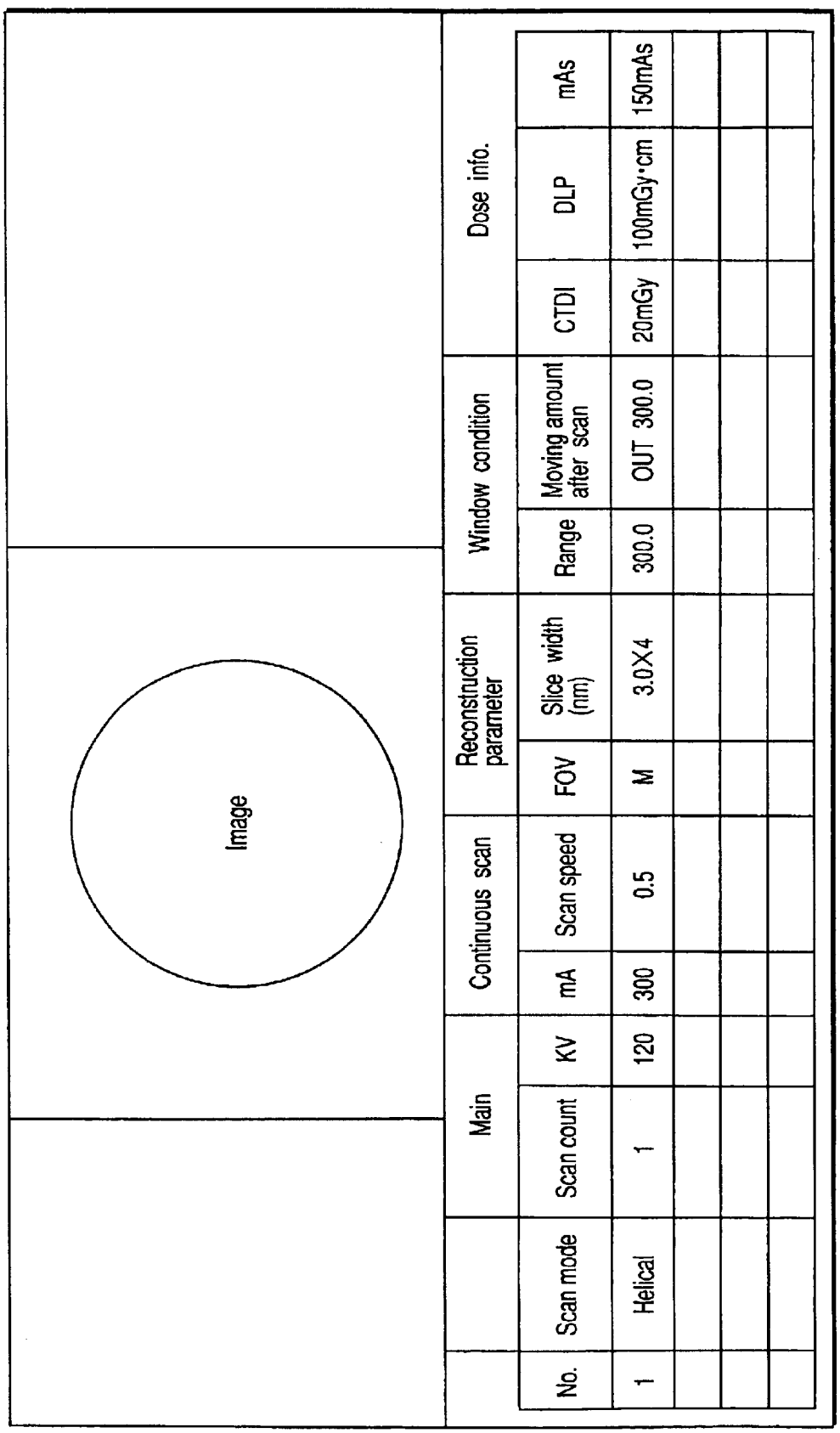
FIG. 9 is a view showing an example of the display form of imaging conditions, CTDI and the like, and a total radiation dose.

These calculated indexes are displayed on the LED 11 in a predetermined form (see FIG. 9). Each index is displayed in the form that can be associated with the parameters set on an examination window. If an examination can be done by a combination of the above scan and another scan such as a helical scan or conventional scan (i.e., a plurality of types of scans can be grouped), the accumulated value obtained by these scans is displayed.

(Absorptance Map)

This X-ray CT apparatus forms at least one scanogram and generates an X-ray absorptance map for each object to be examined on the basis of this scanogram. Generation of this X-ray absorptance map will be described below.

First of all, scanography is executed throughout the scan range shown in FIG. 5 to obtain one scanogram. In this case, a scanography in the X-ray CT apparatus is generally executed before tomography to perform positioning and determine imaging conditions for tomography. The image acquired with the scanography is called scanogram. More specifically, for example, scanography is executed as follows. The position of the X-ray tube is fixed to a given rotational angle (e.g., to face the front side of the object). In this state, the object is translated in the body axis direction while being irradiated with X-rays, and the two-dimensional amount of X-rays transmitted through the object throughout the scan range is detected, thereby forming a scanogram. Note that in this scanography, the high voltage generating section 5 supplies constant tube voltage and tube current to the X-ray tube 2.

FIG. 6 is a view schematically showing an acquired scanogram. In the scanogram shown in FIG. 6, scan counts (sc1 to scm) are written in the body axis direction of the object P, and the channel counts (ch1 to chn) of detection elements constituting the X-ray detector 4 are written in the body width direction of the object P in correspondence with the projection data of the scanogram (to be referred to as a "scanogram PJ" hereinafter).

The data acquisition section 9 acquires the data of the amount of X-rays transmitted on a channel basis. The acquired data are supplied to the scanogram generating section 12. The scanogram generating section 12 generates the scanogram PJ on the basis of the supplied data.

The scanogram PJ from the scanogram generating section 12 or the data of the amount of X-rays transmitted acquired on a channel basis by the data acquisition section 9 is supplied to the pattern computing section 13. In addition, the data acquired by executing the scanography in a state wherein the object is not arranged are also supplied to the scanogram generating section 12. This data is a scanogram with respect to air phantom and is to be referred to as a "air calibration data". The pattern computing section 13 generates an absorptance map in the following manner from the air calibration data and the data supplied from the data acquisition section 9 or the like.

First of all, the pattern computing section 13 divides the data supplied from the data acquisition section 9 or the scanogram PJ into matrixes. Similarly, the pattern computing section 13 divides the air calibration data into matrixes. A matrix is a basic unit for the calculation of X-ray absorptance and formed from at least one detection element. FIG. 6 shows an example in which one matrix is defined by the contours between one slice width and one channel. However, the present invention is not limited to this. For the sake of a specific description, this embodiment will exemplify the case wherein one matrix is defined by the contours between one slice width and one channel.

The pattern computing section 13 calculates an X-ray absorptance in each matrix of the data supplied from the data acquisition section 9 or the scanogram PJ on the basis of the amount of X-rays of each matrix of the air calibration data to generate an absorptance map. Let Iin be the amount of X-rays of a predetermined matrix of the air calibration data, Tout be the amount of X-rays detected in the matrix the scanogram PJ or the like corresponding to the predetermined matrix of the air calibration data, $\mu$ be an X-ray absorptance (the ratio of X-ray energy absorbed when X-rays are transmitted through a substance with a unit thickness), and t be the thickness of the object. In this case, Iout=Iin·exp[$-\mu$t] is established between Iin and Iout. An absorptance in this matrix can be obtained by solving this equation with respect to $\mu$.

FIG. 7 is a graph showing X-ray absorptances in the respective matrixes corresponding to scn. By calculating an X-ray absorptance in each matrix in scan in the entire scan range in this manner, an X-ray absorptance distribution on a matrix basis in the scan range, i.e., an absorptance map, is generated.

In the above case, the absorptance map is generated from the data supplied from the data acquisition section 9 or the scanogram PJ. However, the present invention is not limited to this. For example, an absorptance map may be generated from scanogram data obtained after image reconstruction done on the basis of the scanogram PJ.

In the above case, the X-ray absorptances in all the matrixes are computed by obtaining X-ray absorptances in the respective channels in the respective slices. In contrast to this, the X-ray absorptances in all the matrixes may be computed by interpolation processing that uses discretely obtained X-ray absorptances in matrixes. Alternatively, the X-ray absorptances in all the matrixes may be computed on the basis of the correlation between the X-ray absorptances obtained in the respective channels in a given slice.

In addition, an absorptance map may be generated by using a plurality of scanograms in different directions. This makes it possible to correct the difference between the body axis of the object and rotation center axis of the X-ray tube 2 in terms of data.

Alternatively, the X-ray absorptances in all the matrixes may be computed by using the X-ray amount detected by the compensatory detector 3 before transmitting through the object P, instead of the air calibration data.

Furthermore, a similar object can be achieved by using, for example, an absorbed dose map on a matrix basis instead of an absorptance map on a matrix basis. In this case, an absorbed dose on a matrix basis can be obtained from $\mu$t.

(Determination of Imaging Condition)

Determination of an imaging condition by using the above X-ray absorptance map, which is determined to reduce the radiation dose to an object to be examined and improve the quality of tomographic images, will be described next.

An imaging condition is determined in accordance with the position of the X-ray tube 2 in the body axis direction of the object P and the angular direction (view direction) with respect to the body axis by approximately calculating the diameter of a virtual phantom substantially equivalent to the object P. In this case, the imaging condition includes at least one of conditions required for imaging, e.g., the tube voltage and current in the X-ray tube 2, the rotational speed of the rotating ring of the gantry 1, the size of each detection element of the detector 4, the helical pitch, and the scan range, regardless of whether they are set by the operator. For the sake of a specific description, this embodiment will exemplify the case wherein a proper X-ray emission amount pattern (control pattern for the tube current in the X-ray tube 2) is determined on the basis of the above X-ray absorptance map and the tube voltage in the X-ray tube 2, the helical pitch, the scan range, and the like which are input by the operator.

First of all, the pattern computing section 13 obtains the thickness of the object P on the front side on a channel basis (i.e., a matrix basis) in each scan from the X-ray absorptances detected by the X-ray detection elements constituting each channel. For example, this thickness can be obtained by calculating a water phantom substantially equivalent to the object P and regarding the calculated thickness as the thickness of the object P. More specifically, a proportional calculation is performed with respect to the correction value determined from the relationship between the thickness of the object P on the front side and the thickness of water equivalent to the object, and the calculated value is regarded as the virtual thickness of the object P.

Note that in this calculation, the sum or average of the X-ray absorptances in a plurality of adjacent channels (a plurality of adjacent matrixes) of the X-ray detector 4 may be regarded as a unit X-ray absorptance at that position. Alternatively, the sum or average of the X-ray absorptances in a plurality of matrixes adjacent to each other in the channel and scan directions may be regarded as a unit X-ray absorptance at that position.

The pattern computing section 13 then adds up the X-ray absorptances on a matrix basis in each of scans Sc1 to Scm in the horizontal direction (channel direction). That is, the X-ray absorptances detected by all the detection elements ch1 to chn are added up in each of scans sc1 to scm. The pattern computing section 13 calculates the thickness of a water phantom substantially equivalent to the object P in the body width direction and regards this thickness as the thickness of the object P in the body width direction.

In this case as well, the sum or average of the X-ray absorptances in a plurality of matrix arrays in the scan direction may be set as an X-ray absorptance in the body width direction at that position. The material for a phantom is not limited to water. Any material that can be used for CT value measurement, e.g., polypropylene, can be used.

The ratio of the thickness in the body width direction to the thickness on the front side is calculated in each scan to obtain a virtual water phantom having an elliptic cross-section substantially equivalent to a cross-section of the object P. By stacking such phantoms in the body axis direction throughout the scan range, a water phantom having an elliptic cross-section substantially equivalent to the object P is obtained.

A tube current pattern is so determined as to set a proper X-ray emission amount in accordance with the position of this water phantom in the body axis direction and the angular direction of the phantom with respect to the body axis. That is, the length of the path of X-rays transmitted through the phantom changes depending on the size of the water phantom. The X-ray absorptance also changes depending on the path. Therefore, a tube current pattern for the X-ray tube 2 is generated in consideration of the X-ray path of a water phantom at each rotational angle in scan such that graininess caused by noise in images, i.e., an image standard deviation (image SD), is made uniform.

Assume that X-rays are emitted with a tube current Ia at a position A of the phantom in the scan direction. Let DPa be the maximum depth of the phantom around the body axis, and DPb be the maximum thickness of the phantom at a position B upon rotation of the X-ray tube 2. In this case, in order to obtain tomographic images of the same image SD at the positions A and B, a tube current Ib at the position B may be set as follows:

$$Ib = Ia * \exp(-\mu DPa) / \exp(-\mu DPb)$$

where $\mu$ is the X-ray absorptance of water. The pattern computing section 13 generates a tube current pattern by computing a tube current corresponding to the position of the phantom in the body axis direction and the rotational angle throughout the scan range. The generated tube current pattern is stored in the pattern storage section 14.

In practice, the tube current pattern may be changed in the body axis direction of the object P for each scan or a plurality of scans. Likewise, the tube currents may be switched for each angle (e.g., 90°) at which the X-ray dose greatly changes in the angular direction of the object P with respect to the body axis, for example, when a cross-section of the object P is regarded as an ellipse, the major-axis direction or minor axis direction of the ellipse.

Figure 8:
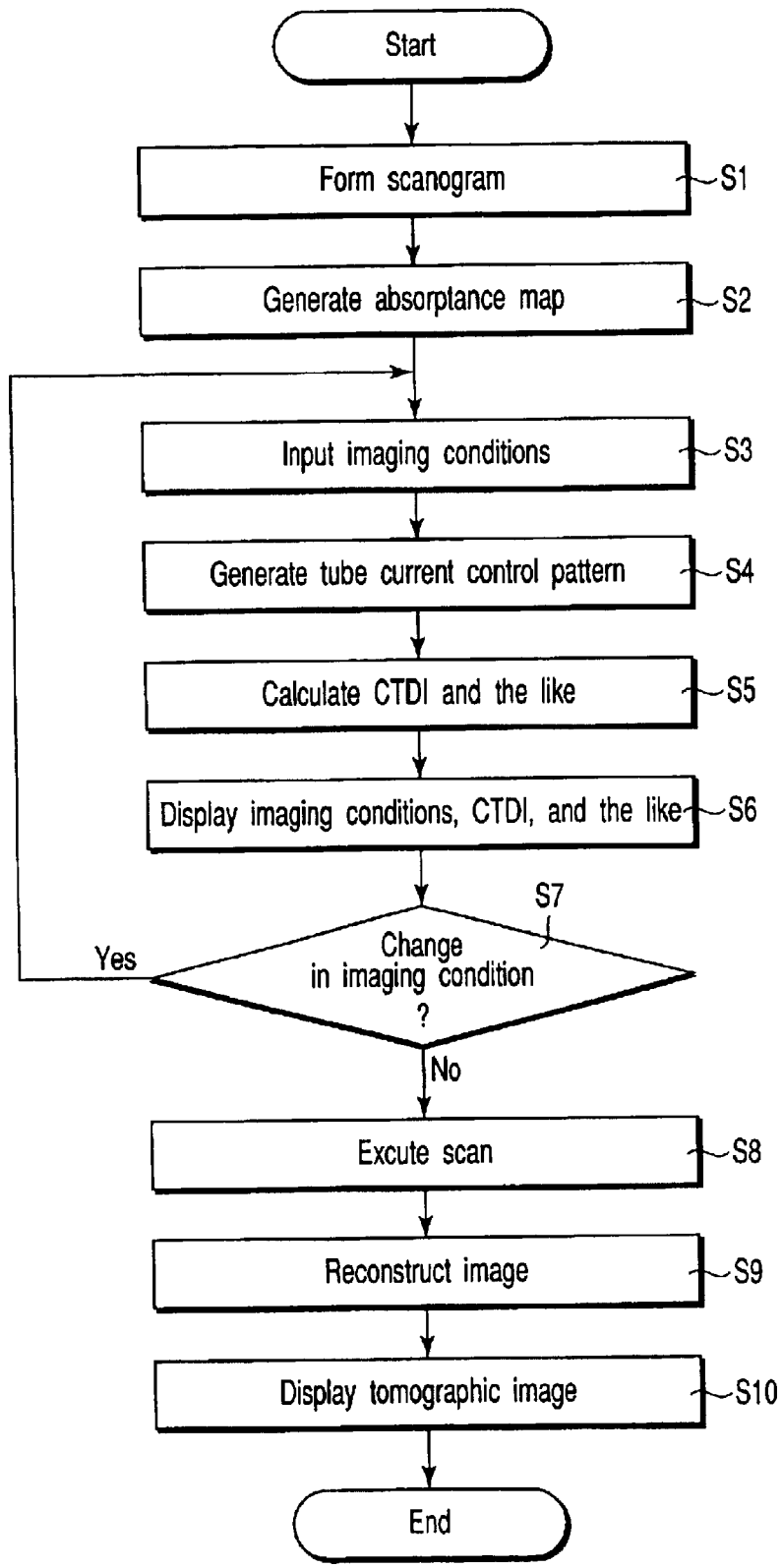
FIG. 8 is a flow chart showing the flow of processing in a case wherein the X-ray CT apparatus performs helical scan.

The operation of this X-ray CT apparatus will be described next by exemplifying helical scan. FIG. 8 is a flow chart showing the flow of processing in a case wherein the X-ray CT apparatus performs helical scan. As shown in FIG. 8, first of all, a scanogram of the object in one direction is formed by scanography (step S1).

An absorptance map is generated by the above method on the basis of the scanogram (step S2). The operator inputs imaging conditions such as a tube voltage in the X-ray tube 2, a helical pitch, a scan range, an imaging slice thickness on the isocenter and the like (step S3).

The pattern computing section 13 generates a tube current control pattern for the X-ray tube 2 on the basis of the input tube voltage in the X-ray tube 2 and the like and the X-ray absorptance map (step S4).

The X-ray amount calculating section 17 then calculates CTDI and the like on the basis of the imaging conditions including the generated tube current control pattern (step S5). The calculated CTDI and the like and the imaging conditions are displayed on the display section 11 (step S6).

FIG. 9 is a view showing an example of the display form of imaging conditions and total radiation doses such as a CTDI. As shown in FIG. 9, CTDI, DLP, and mAs as indexes representing radiation doses and imaging conditions are displayed, together with an image such as a scanogram, in the form that allows the operator to recognize the progress of an examination. This allows the operator to visually check imaging conditions, indexes representing radiation doses, and the like.

It is checked whether the displayed imaging conditions are changed (step S7). If the imaging conditions are to be changed, operation in steps S3 to S6 is repeated. If the imaging conditions are not changed, helical scan for tomography is executed as follows in accordance with the tube current control pattern generated in step S4 and other imaging conditions (step S8).

The rotating/driving section 6 rotates the X-ray tube 2 and X-ray detector 4 around the object P by using the rotating ring under the control of the system control section 15. The bed driving section 8 translates the bed 7 on which the object P is placed at a constant speed in the body axis direction under the control of the system control section 15. As a consequence, the X-ray tube 2 rotates while emitting X-rays around the object P, thereby performing helical scan. At this time, the amount of X-rays before they are transmitted through the object P is detected by the compensatory detector 3, and the amount of X-rays transmitted through the object P is detected by the X-ray detector 4. The X-ray amount detected by the X-ray detector 4 is acquired as X-ray transmission data by the data acquisition section 9.

In the helical scan, the system control section 15 controls the high voltage generating section 5 on the basis of the tube current control pattern for the X-ray tube 2 which is stored in the pattern storage section 14. The high voltage generating section 5 supplies a tube current to the X-ray tube 2 in accordance with the position of the X-ray tube 2 in the body axis direction and the angle of the X-ray tube 2 with respect to the body axis. Assume that the tube voltage applied to the X-ray tube 2 is constant. The X-ray tube 2 irradiates the object P with the amount of X-rays based on the tube voltage and tube current supplied in accordance with the position of the X-ray tube 2 in the body axis of the object P and the angle of the X-ray tube 2 with respect to the body axis.

The transmission data acquired by the data acquisition section 9 are supplied to the image reconstructing section 10, which in turn performs image reconstruction processing on the basis of the transmission data (step S9). The reconstructed image is displayed as a tomographic image on the display section 11 (step S10).

As described above, according to this X-ray CT apparatus, an absorptance map is generated from a scanogram at least in one direction, and imaging conditions are determined on the basis of the absorptance map so as to reduce the radiation dose and image standard deviation. Since tomography is executed in accordance with these imaging conditions, the X-ray dose to the object is reduced, and a tomographic image with good image quality can be obtained. When tube current control is to be performed in accordance with the position of the X-ray tube in the body axis direction of the object and the angle of the X-ray tube with respect to the body axis, the precision of tube current control can be improved.

The above embodiment has exemplified the helical scan. However, the present invention is not limited to this. For example, an absorptance map can be generated and imaging conditions can be determined on the basis of the absorptance map so as to reduce the radiation dose and image standard deviation in, for example, multi-scan in which tomographic images of a plurality of slices are obtained by one scan, dynamic scan in which CT fluoroscopy, brain blood flow measurement, or the like is performed, scan such as CT fluoroscopy or Real Prep including intermittent X-ray emission, and the like, not to mention operation of obtaining tomographic images of a plurality of regions (slices) in one routine.

According to this X-ray CT apparatus, an index representing a radiation dose and the like in tomography are calculated and displayed on the basis of imaging conditions before the execution of scan. In addition, the index representing the radiation dose and the like in tomography are calculated and displayed in the case where the imaging condition includes a current value of the X-ray tube which is varied in accordance with a position of the X-ray source in a body axis direction and a rotation angle centered on the body axis of the object, in such a manner that each standard deviation of computer tomography to be acquired is made uniform. The operator can therefore know an accurate radiation dose before tomography, and can arbitrarily change imaging conditions as needed. In addition, according to this X-ray CT apparatus, since an index representing a radiation dose is updated and displayed every time imaging conditions are changed, the operator can quickly grasp an index representing a radiation dose and the like associated with scan to be executed.

(Second Embodiment)

An X-ray CT apparatus according to the second embodiment will be described next. The X-ray CT apparatus according to this embodiment is designed to determine the size of a object P to be examined on the basis of a scanogram formed before tomography and adjust the amount of X-rays emitted in tomography in accordance with the size of the object. For the sake of a specific description, this embodiment will exemplify a case wherein whether the object P is a child or not is determined on the basis of an absorptance map obtained from a scanogram, and the amount of X-ray emitted in tomography is adjusted in accordance with the determination. However, the present invention is not limited to this. For example, an object size can be directly determined on the basis of the CT values from the respective detection elements, which form a scanogram, and the amount of X-rays emitted in tomography can be adjusted in accordance with the size.

The arrangement of the X-ray CT apparatus according to this embodiment is almost the same as that shown in FIGS. 4 and 5.

Figure 10:
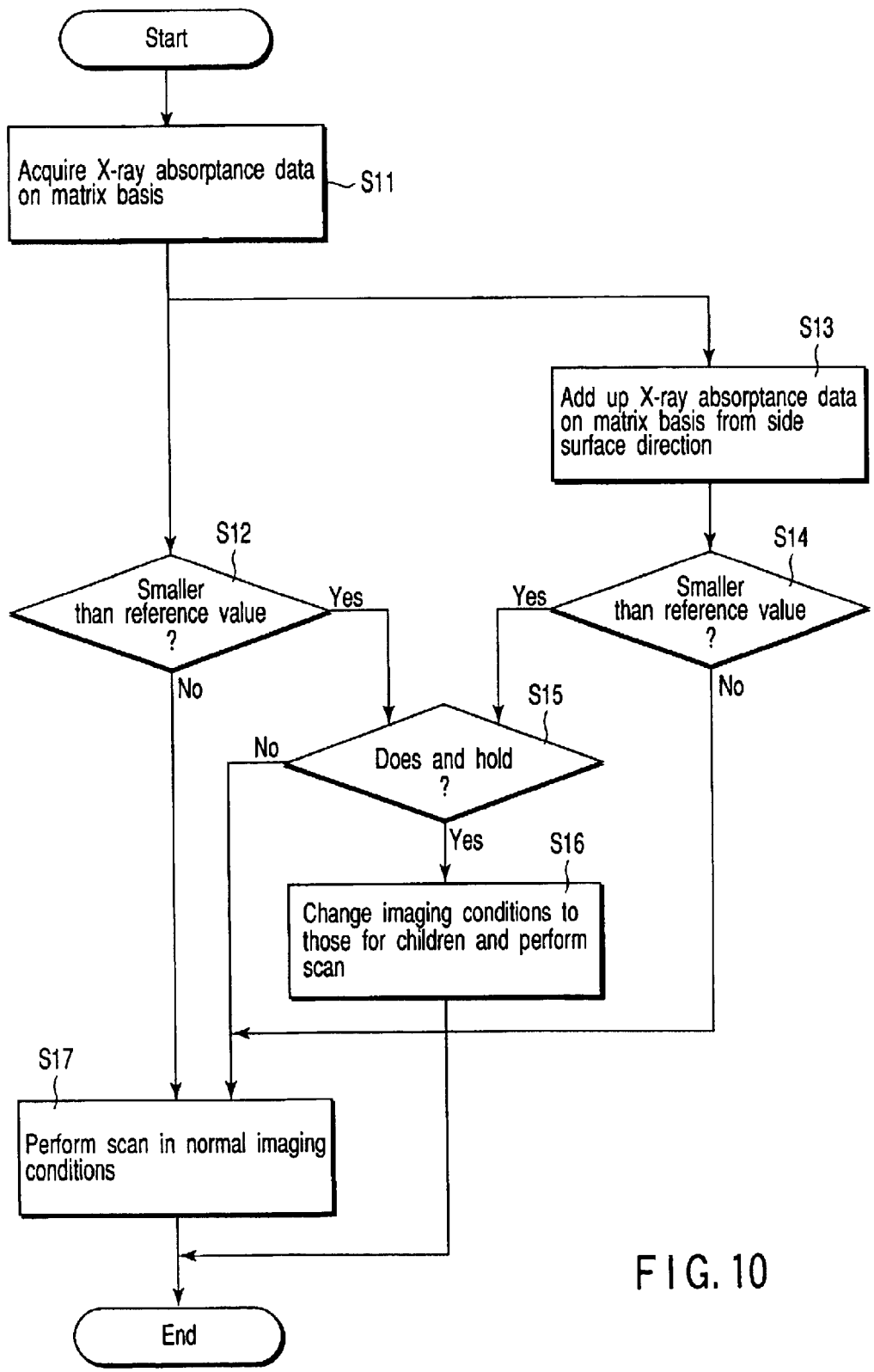
FIG. 10 is a flow chart for processing to be executed by an X-ray CT apparatus according to the second embodiment in tomography.

FIG. 10 is a flow chart of processing to be executed by the X-ray CT apparatus according to this embodiment in tomography. As shown in FIG. 10, first of all, a pattern computing section 13 obtains an X-ray absorptance in each channel in each slice (i.e., an X-ray absorptance on a matrix basis) from the transmission X-ray amount data acquired by a data acquisition section 9 (step S11).

The pattern computing section 13 then determines whether the absorptance in each matrix is less than a predetermined reference value (step S12). This determination on the absorptance in each matrix is equivalent to determining whether the thickness of the object P from the front side is smaller than a reference thickness. If the X-ray absorptance exceeds the reference value, it is known that the thickness of the object P is larger than the reference thickness. If the X-ray absorptance is equal to or less than the reference value, it is known that the thickness of the object P is smaller than the reference thickness.

The X-ray absorptances on a matrix basis are then added up from the side surface direction (channel direction) of the object (step S13). That is, the sum of X-ray absorptances in all the matrixes is obtained in each scan direction.

The pattern computing section 13 determines whether the obtained cumulative value of X-ray absorptances in each scan is smaller than a predetermined reference value (step S15). This determination is equivalent to determining whether the width of the object P along the side surface direction is smaller than the reference thickness. If the cumulative value exceeds the reference value, it is known that the width of the object P is larger than the reference value. If the cumulative value is equal to or less than the reference value, it is known that the width of the object P is smaller than the reference value.

The pattern computing section 13 determines whether the AND of the determination results obtained in steps S12 and S14 holds (step S15). If the AND holds, the pattern computing section 13 determines that the object P is a child whose body thickness and body width are smaller than the respective reference values or an object that requires a reduction in radiation dose.

In this case, a system control section 15 preferably display, on the data acquisition section 9, a message that prompts the operator to change imaging conditions for a reduction in radiation dose. Alternatively, a sound or the like may be generated to inform the operator of the same message. In addition, the system control section 15 controls a high voltage generating section 5 to reduce at least one of a tube voltage and a tube current, thus changing imaging conditions in accordance with the child (step S16). This makes it possible to automatically reduce the X-ray dose in accordance with the size of an object to be examined.

If the pattern computing section 13 determines NO in steps S12 and S14 or the AND of the determination results obtained in steps S12 and S14 does not hold, the section executes scan under normal imaging conditions (step S17).

Note that step S12 may be omitted from the above series of operations, and it may be determined only from the operation in step S14, in which only the cumulative X-ray absorptance data on a matrix basis in each scan is compared with a given reference value, whether the object is a child or an object that requires a reduction in radiation dose. Alternatively, the size of a phantom equivalent to the human body is virtually obtained by the method described in the first embodiment on the basis of the X-ray absorptances obtained in steps S11 and S13, and whether the object is a child may be determined by comparing the obtained size with a given reference value.

In the above embodiment, when it is determined that the object is a child, the imaging conditions are automatically changed to those for a child. In contrast to this, the embodiment may be designed to display, on the data acquisition section 9, a message that prompts the operator to change the imaging conditions to those for a child (low radiation dose), when it is determined that the object is a child, instead of automatically changing the imaging conditions. Furthermore, as in the first embodiment, an index representing a radiation dose and the like may be displayed, and imaging conditions may be obtained from an absorptance map.

In a general X-ray CT apparatus, imaging conditions as initial settings for adults greatly differ from those for children. For example, adults may be imaged with a tube current of 200 mA, whereas newborn baby or children may be imaged with a tube current of 30 mA. In contrast to this, in the X-ray CT apparatus according to this embodiment, an imaging condition, e.g., a tube current, is controlled to a value for a reduction in radiation dose in accordance with the size of an object to be examined. This makes it possible to take effective measures to reduce a radiation dose for an object with a small size, e.g., a child. Such measures to reduce a radiation dose in accordance with the size of an object to be examined are especially effective in the execution of helical scan in which the radiation dose tends to be large.

While present invention has been described on the basis of the respective embodiments, it will be obvious to those skilled in the art that various changes and modifications may be made within the technical category of the invention. It is therefore to be understood that such changes and modifications fall within the spirit and scope of the invention.

In addition, the respective embodiments can be properly combined where possible. In this case, effects of the combinations can be obtained. Furthermore, the above embodiments include inventions of various stages, and various inventions can be extracted by proper combinations of a plurality of disclosed constituent elements. When, for example, at least one of the problems described in "BACKGROUND OF THE INVENTION" can be solved and at least one of the effects described in "BRIEF SUMMARY OF THE INVENTION" can be obtained even if several constituent elements are omitted from the all the constituent elements in each embodiment, the arrangement from which these constituent elements are omitted can be extracted as an invention.

What is claimed is:

1. An X-ray computer tomography apparatus comprising:
   an X-ray source which emits X-rays;
   an X-ray detector which has a plurality of detection elements configured to detect X-rays transmitted through an object to be examined;
   a scanogram generating section which generates a scanogram of the object on the basis of an output from said X-ray detector;
   a distribution information generating section which generates distribution information of X-ray absorptances or absorbed X-ray doses in a first direction by dividing the scanogram in matrixes and calculating X-ray absorptances or absorbed X-ray doses on a matrix basis, and in a second direction different from the first direction by adding X-ray absorptances or absorbed X-ray doses on a matrix basis in the second direction;
   an imaging condition determining section configured to determine the imaging condition on the basis of the distribution information in the first and second directions; and
   a controller which controls computer tomography of the object on the basis of the imaging condition.

2. The apparatus according to claim 1, further comprising:
   an X-ray amount calculating section which calculates a radiation dose to the object or a total amount of X-rays emitted from said X-ray source on the basis of the imaging condition; and
   a display device which displays the calculated radiation dose or the total X-ray amount.

3. An X-ray computer tomography apparatus comprising:
   an X-ray source configured to emit X-rays;
   an X-ray detector which has a plurality of detection elements configured to detect X-rays transmitted through an object to be examined;
   a scanogram generating section configured to generate a scanogram of the object on the basis of an output from said X-ray detector;
   a distribution information generating section configured to generate distribution information of X-ray absorptances or absorbed X-ray doses in a first direction of the object by dividing the scanogram into matrixes;
   an imaging condition determining section configured to determine an imaging condition on the basis of the distribution information and determine a size of the matrix in accordance with an imaging slice thickness or imaging slice width; and
   a controller configured to controls computer tomography of the object on the basis of the imaging condition.

4. The apparatus according to claim 3, further comprising:
   an X-ray amount calculating section which calculates a radiation dose to the object or a total amount of X-rays emitted from said X-ray source on the basis of the imaging condition; and
   a display device which displays the calculated radiation dose or the total X-ray amount.

5. An X-ray computer tomography apparatus comprising:

an X-ray source configured to emit X-rays;

an X-ray detector which has a plurality of detection elements configured to detect X-rays transmitted through an object to be examined;

a scanogram generating section configured to generate a scanogram of the object on the basis of an output from said X-ray detector;

a distribution information generating section configured to generate distribution information of X-ray absorptances or absorbed X-ray doses in a first direction of the object by dividing the scanogram into matrixes;

an imaging condition determining section configured to determine an current value supplied to said X-ray source on the basis of the distribution information; and a controller configured to control computer tomography of the object such as to change the current value supplied to said X-ray source in accordance with movement of said X-ray source on the basis of the imaging condition.

6. The apparatus according to claim 5, further comprising:

an X-ray amount calculating section which calculates a radiation dose to the object or a total amount of X-rays emitted from said X-ray source on the basis of the imaging condition; and a display device which displays the calculated radiation dose or the total X-ray amount.

7. An X-ray computer tomography apparatus comprising:

an X-ray source configured to emit X-rays;

an X-ray detector which has a plurality of detection elements configured to detect X-rays transmitted through an object to be examined;

a scanogram generating section configured to generate a scanogram of the object on the basis of an output from said X-ray detector;

an imaging condition determining section configured to determine an imaging condition associated with computer tomography of the object on the basis of a scanogram in a first direction of the object, the imaging condition including a current value of said X-ray source which is varied in accordance with a position of said X-ray source in a body axis direction and a rotation angle centered on the body axis of the object, in such a manner that each standard deviation of computer tomography to be acquired is made uniform;

an X-ray amount calculating section configured to calculate a radiation dose to the object or a total amount of X-rays emitted from said X-ray source on the basis of the imaging condition; and a display device configured to display the calculated radiation dose or the total X-ray amount.

* * * * *